(12) United States Patent
Lowy et al.

(10) Patent No.: US 7,465,446 B2
(45) Date of Patent: Dec. 16, 2008

(54) SURROGATE THERAPEUTIC ENDPOINT FOR ANTI-CTLA4-BASED IMMUNOTHERAPY OF DISEASE

(75) Inventors: Israel Lowy, Dobbs Ferry, NY (US); Geoffrey M. Nichol, Short Hills, NJ (US)

(73) Assignee: Medarex, Inc., Princeton, NJ (US)

( * ) Notice: Subject to any disclaimer, the term of this patent is extended or adjusted under 35 U.S.C. 154(b) by 569 days.

(21) Appl. No.: 10/857,749

(22) Filed: May 27, 2004

(65) Prior Publication Data

US 2004/0241169 A1    Dec. 2, 2004

Related U.S. Application Data

(60) Provisional application No. 60/475,067, filed on May 30, 2003.

(51) Int. Cl.
*A61K 39/395* (2006.01)
*C07K 16/00* (2006.01)
*C07K 16/28* (2006.01)

(52) U.S. Cl. .............. 424/130.1; 424/141.1; 424/143.1; 424/144.1; 530/387.1; 530/388.1; 530/388.2; 530/388.22

(58) Field of Classification Search ........................ None
See application file for complete search history.

(56) References Cited

U.S. PATENT DOCUMENTS

| | | | |
|---|---|---|---|
| 5,811,097 A | 9/1998 | Allison et al. |
| 5,855,887 A | 1/1999 | Allison et al. |
| 6,051,227 A | 4/2000 | Allison et al. |
| 6,682,736 B1 | 1/2004 | Hanson et al. |
| 2002/0039581 A1 | 4/2002 | Carreno et al. |
| 2002/0086014 A1 | 7/2002 | Korman et al. |

FOREIGN PATENT DOCUMENTS

| WO | WO-00/37504 A2 | 6/2000 |
| WO | WO-01/14424 A2 | 3/2001 |

OTHER PUBLICATIONS

Beck et al., J. Clin. Oncol., 2006, 24: 2283-2289.*
Cancer Therapy Evaluation Program, Common Terminology Criteria for Adverse Events (CTCAE), Version 3.0, DCTD, NCI, NIH, DHHS, Mar. 31, 2003 (provided by Applicant).*
Janik et al., "A Pilot Study Of MDX-010 After Vaccine Failure In Patients With Advanced Malignacy," Blood, vol. 102, No. 11, p. 647A, Nov. 16, 2003.
Phan et al., "Cancer Regression And Autoimmunity Induced By Cytotoxic T Lymphocyte-Associated Antigen 4 Blockade In Patients With Metastatic Melanoma," Proceedings Of The National Academy Of Sciences Of USA, vol. 100, No. 14, pp. 8372-8377, Jul. 8, 2003.

International Search Report for PCT/US2004/016995, mailed May 10, 2005.
Van Elsas et al. Elucidating the autoimmune and antitumor effector mechanism of a treatment based on cytotoxic T lymphocyte antigen-4 blockade in combination with B16 melanoma vaccine: comparison of prophylaxis and therapy. J. Exp. Med. Aug. 20, 2001,V. 194, pp. 481-489, especially abstract, p. 482.
Chambers, Cynthia A., et al., "Lymphoproliferation in CTLA-4-Deficient Mice is Mediated by Costimulation-Dependent Activation of CD4+ T Cells", Immunity, Dec. 1997, vol. 7, pp. 885-895.
Chambers, Cynthia A., et al., "Co-stimulation in T cell responses", Curr. Opin. Immunol., 1997, vol. 9, pp. 396-404.
Hurwitz, Arthur A., et al., "CTLA-R blockade synergizes with tumor-derived granulocyte-macrophage colony-stimulating factor for treatment of an experimental mammary carcinoma", Proc. Natl. Acad. Sci., Aug. 1998, pp. 10067-10071.
Hurwitz, Arthur A., et al., "Immunotherapy of Primary Prostate Cancer in a Transgenic Model Using a Combination of CTLA-4 Blockade and Tumor Cell Vaccine", Cancer Research, May 1, 2000, vol. 60, pp. 2444-2448.
Damle, Nitin K., et al., "Alloantigen-Specific Cytotoxic and Suppressor T Lymphocytes are Derived from Phenotypically Distinct Precursors", The Journal of Immunology, Nov. 1983, vol. 131, No. 5, pp. 2296-2300.
Kearney, Elizabeth R., et al., "Antigen-dependent Clonal Expansion of a Trace Population of Antigen-Specific CD4+ T Cells in Vivo is Dependent on CD28 Costimulation and Inhibited by CTLA-41", The Journal of Immunology, 1995, vol. 155, pp. 1032-1036.
Leach, Dana R., et al., "Enhancement of Antitumor Immunity by CTLA-4 Blockade", Science, Mar. 22, 1996, vol. 271, pp. 1734-1736.
Lindsten, Tullia, et al., "Regulation of Lymphokine Messenger RNA Stability by a Surface-Mediated T Cell Activation Pathway", Science, Apr. 21, 1989, vol. 244, pp. 339-343.
Luhder, Fred, et al., "Cytotoxic T Lymphocyte-associated Antigen 4 (CTLA-4) Regulates the Unfolding of Autoimmune Diabetes", J. Exp. Med., Feb. 2, 1998, vol. 187, No. 3, pp. 427-432.
Overwijk, Willem M., et al., "Vaccination with a recombinant vaccinia virus encoding a "self" antigen induces autoimmune vitiligo and tumor cell destruction in mice: Requirement for CDR+ T lymphocytes", Proc. Natl. Acad. Sci., Mar. 1999, vol. 96, pp. 2982-2987.
Matsui, Toshihiro, et al., "Autoantibodies to T Cell Costimulatory Molecules in Systemic Autoimmune Diseases", The Journal of Immunology, 1999, vol. 162, pp. 4328-4335.
Perrin, Peter J., et al., "CTLA-4 Blockade Enhances Clinical Disease and Cytokine Production During Experimental Allergic Encephalomyelitis 1,2", The Journal of Immunology, vol. 157, pp. 1333-1336.

(Continued)

*Primary Examiner*—Ilia Ouspenski
(74) *Attorney, Agent, or Firm*—Baker Botts L.L.P.

(57) ABSTRACT

The present invention provides a method of treatment using human sequence antibodies against human CTLA-4. In particular, methods of treating cancer are provided.

19 Claims, No Drawings

OTHER PUBLICATIONS

Rosenberg, Steven A., et al., "Vitiligo in Patients with Melanoma: Normal Tissue Antigens Can Be Targets for Cancer Immunotherapy", Journal of Immunotherapy, vol. 19, No. 1, pp. 81-84.

Thompson, Craig B., et al., "CD28 activation pathway regulates the production of multiple T-cell-derived lymphokines/cytokines", Proc. Natl. Acad. Sci., Feb. 1989, vol. 86, pp. 1333-1337.

Van Elsas, Andrea, et al., "Combination Immunotherapy of B16 Melanoma Using Anti-Cytotoxic T Lymphocyte-associated Antigen 4 (CTLA-4) and Granulocyte/Macrophage Colony-Stimulating Factor (GM-CSF)-producing Vaccines Induces Rejection of Subcutaneous and Metastatic Tumors Accompanied by Autoimmune Depigmentation", J. Exp. Med., Aug. 2, 1999, vol. 190, No. 3, pp. 355-366.

Walunas, Theresa L., et al., "CTLA-4 Can Function as a Negative Regulator of T Cell Activation", Immunity, Aug. 1994, vol. 1, pp. 405-413.

* cited by examiner

SURROGATE THERAPEUTIC ENDPOINT FOR ANTI-CTLA4-BASED IMMUNOTHERAPY OF DISEASE

CROSS-REFERENCE TO RELATED APPLICATIONS

This application claims priority to U.S. provisional application Ser. No. 60/475,067, filed on May 30, 2003, the contents of which are hereby incorporated in their entirety.

FIELD OF THE INVENTION

The present invention relates generally to molecular immunology and the treatment of human diseases. In particular, it relates to refined treatment methods using antibodies against human CTLA-4.

BACKGROUND OF THE INVENTION

The vertebrate immune system requires multiple signals to achieve optimal immune activation (see, e.g., Janeway, Cold Spring Harbor Symp. Quant. Biol. 1989; 54:1-14; Paul William E., ed. Raven Press, N.Y., Fundamental Immunology, 4th edition (1998), particularly chapters 12 and 13, pages 411 to 478). Interactions between T lymphocytes (T cells) and antigen presenting cells (APC) are essential to the immune response. Levels of many cohesive molecules found on T cells and APC's increase during an immune response (Springer et al., A. Rev. Immunol. 1987; 5:223-252; Shaw and Shimuzu, Current Opinion in Immnunology, 1988 Eds. Kindt and Long, 1:92-97; and Hemler, Immunology Today 1988; 9:109-113). Increased levels of these molecules may help explain why activated APC's are more effective at stimulating antigen-specific T cell proliferation than are resting APC's (Kaiuchi et al., J. Immunol. 1983; 131:109-114; Kreiger et al., J. Immunol. 1985; 135:2937-2945; McKenzie, J. Immunol. 1988; 141:2907-2911; and Hawrylowicz and Unanue, J. Immunol. 1988; 141:4083-4088).

T cell immune response is a complex process that involves cell-cell interactions (Springer et al., A. Rev. Immunol. 1987; 5:223-252), particularly between T and accessory cells such as APC's, and production of soluble immune mediators (cytokines or lymphokines) (Dinarello, New Engl. J. Med 1987; 317:940-945; Sallusto, J. Exp. Med. 1997; 179:1109-1118). This response is regulated by several T-cell surface receptors, including the T-cell receptor complex (Weiss, Ann. Rev. Immunol. 1986; 4:593-619) and other "accessory" surface molecules (Allison, Curr. Opin. Immunol. 1994; 6:414-419; Springer, 1987, supra). Many of these accessory molecules are naturally occurring cell surface differentiation (CD) antigens defined by the reactivity of monoclonal antibodies on the surface of cells (McMichael, Ed., *Leukocyte Typing III*, Oxford Univ. Press, Oxford, N.Y., 1987).

CD28 antigen, a homodimeric glycoprotein of the immunoglobulin superfamily (Aruffo and Seed, Proc. Natl. Acad. Sci. 1987; 84:8573-8577), is an accessory molecule found on most mature human T cells (Damle et al., J. Immunol. 1983; 131:2296-2300). Current evidence suggests that this molecule functions in an alternative T cell activation pathway distinct from that initiated by the T-cell receptor complex (June et al., Mol. Cell. Biol. 1987; 7:4472-4481). Monoclonal antibodies (MAbs) reactive with CD28 antigen can augment T cell responses initiated by various polyclonal stimuli (reviewed by June et al., supra). These stimulatory effects may result from MAb-induced cytokine production (Thompson et al., Proc. Natl. Acad. Sci 1989; 86:1333-1337; and Lindsten et al., Science 1989; 244:339-343) as a consequence of increased mRNA stabilization (Lindsten et al., 1989, supra).

CTLA-4 is accepted as opposing CD28 activity and dampening T cell activation (Krummel, J. Exp. Med. 1995; 182: 459-465; Krummel et al., Int'l Immunol. 1996; 8:519-523; Chambers et al., Immunity. 1997; 7:885-895). CTLA-4 deficient mice suffer from massive lymphoproliferation (Chambers et al., supra). It has been reported that CTLA-4 blockade augments T cell responses in vitro (Walunas et al., Immunity. 1994; 1:405-413) and in vivo (Kearney, J. Immunol. 1995; 155:1032-1036), exacerbates antitumor immunity (Leach, Science 1996; 271:1734-1736), and enhances an induced autoimmune disease (Luhder, J Exp. Med. 1998; 187:427-432). It has also been reported that CTLA-4 has an alternative or additional impact on the initial character of the T cell immune response (Chambers, Curr. Opin. Immunol. 1997; 9:396-404; Bluestone, J. Immunol. 1997; 158:1989-1993; Thompson, Immunity 1997; 7:445-450). This is consistent with the observation that some autoimmune patients have autoantibodies to CTLA-4. It is possible that CTLA-4 blocking autoantibodies play a pathogenic role in these patients (Matsui, J. Immunol. 1999; 162:4328-4335).

Non-human CTLA-4 antibodies have been used in the various studies discussed above. Furthermore, human antibodies against human CTLA-4 have been described as immunostimulation modulators in a number of disease conditions, such as treating or preventing viral and bacterial infection and for treating cancer (e.g., PCT Publication WO 01/14424 and PCT Publication WO 00/37504). U.S. Pat. No. 5,855,887 discloses a method of increasing the response of a mammalian T cell to antigenic stimulation by combining a T cell with a CTLA-4 blocking agent. U.S. Pat. No. 5,811,097 discloses a method of decreasing the growth of non-T cell tumors by administering a CTLA-4 blocking agent. U.S. patent application Ser. Nos. 09/644,668 and 09/948,939 disclose human CTLA-4 antibodies. Each of these patents and applications is hereby incorporated by reference.

The citation or discussion of any reference in this section or elsewhere in the specification is made only to clarify the description of the present invention and is not an admission that any such reference is "prior art" to any invention described herein.

SUMMARY OF THE INVENTION

The present invention provides a novel method of treating cancer in a patient by administering anti-CTLA-4 antibody to the patient in a dosage sufficient to induce a breakthrough event and detecting the breakthrough event in the patient. In one embodiment the breakthrough event is an autoimmune response to an antigen that exists on non-cancer cells. In another embodiment the breakthrough event is grade 3 or 4. According to the methods of the invention, the breakthrough event is induced by administering escalating dosage amounts of anti-CTLA-4 antibody. In a further embodiment, the breakthrough event is induced by administering anti-CTLA-4 antibody at a reduced dosage interval. In another embodiment, the breakthrough event is a manifestation of non-tumor related autoimmunity. The present invention provides methods for administering a therapeutically effective dosage regimen of anti-CTLA-4 antibody for the treatment of cancer. The invention also provides methods for determining such dosage regimens.

All publications, figures, GenBank Accession references (sequences), ATCC Deposits, patents and patent applications cited herein are hereby expressly incorporated by reference for all purposes to the same extent as if each was so individually denoted.

DETAILED DESCRIPTION

The present invention provides more effective, predictable CTLA-4 antibody-based methods for cancer treatment. The methods of the invention represent a significant development in the treatment of cancers with anti-CTLA-4 antibody because they avoid under-dosing patients with the antibody. A statistically significant correlation between the appearance of an adverse event and response to treatment has been unexpectedly discovered in cancer patients treated with anti-CTLA-4 antibody. Whereas avoidance of serious "adverse events" has been a goal in the treatment of seriously ill cancer patients, the methods of the invention have the goal of inducing and detecting these events (herein termed "breakthrough events" (BE)). The induction of a significant, but reversible, breakthrough event is medically sound in these patients because treatment with a sufficient dose of anti-CTLA-4 antibody may improve the patient's cancer or prolong life.

BE's are acute, dose-related, easily monitored and, to some extent, predictable. BE's can be reversed with drug withdrawal and/or supportive care with or without specific treatment, usually corticosteroid therapy. Administering a dosage of anti-CTLA-4 antibody to induce a BE and detecting the BE is an effective method to treat cancer because of the significant correlation between response to anti-CTLA-4 antibody treatment and the development of a BE.

In a particular embodiment, the anti-CTLA-4 antibody of the present invention is human monoclonal antibody 10D1 as disclosed in WO 01/14424.

The present invention is based, in part, on observations made during clinical testing of a human sequence anti-CTLA-4 antibody in immunotherapy of cancers, as described below. The tests demonstrate the effectiveness of anti-CTLA antibody in the treatment of patients with cancer when a dosage of anti-CTLA-4 antibody sufficient to induce a BE is delivered. According to the invention, anti-CTLA-4 antibody is administered in a dosage sufficient to induce a BE and the BE is detected in the patient.

Various studies led to recognition of a correlation between BE's and anti-tumor efficacy. For example, in cohort 1 of a study, fourteen patients with Stage IV melanoma received anti-CTLA-4 antibody 10D1 (MDX-010) at 3 mg/kg every three weeks for eight weeks in conjunction with vaccination with two gp100 peptides. All patients had prior surgery for their primary tumor. Six patients had prior chemotherapy. Eleven patients had prior immunotherapy. Clinical response was measured by computed axial tomography (CT) and magnetic resonance (MR) imaging. Patient 11, who had prior chemotherapy, had complete resolution of lung, brain and subcutaneous tumors after 5 treatment cycles. Patient 13, who had prior chemotherapy and immunotherapy, had complete resolution of adrenal and lung tumors. Patient 1, who had prior chemotherapy and immunotherapy, was a partial responder. Each of the three responders experienced a grade 3 BE. Patient 1, a partial responder had grade 3 enterocolitis and dermatitis. Patient 1 was treated for autoimmune enterocolitis with IV methylprednisolone, which resulted with marked improvement within 24 hours. Patient 11, a complete responder, had grade 3 hypophysitis and panhypopituitarism. Patient 11 received replacement doses of thyroxine, testosterone and hydrocortisone. Patient 13, a complete responder, had grade 3 dermatitis that resolved upon treatment with hydoxyzine. This study unexpectedly showed that all three responders experienced grade 3 adverse events.

In cohort 2 of the study, twenty-four patients with unresected metastatic melanoma were administered anti-CTLA-4 antibody 10D1 with an initial loading dose of 3 mg/kg and subsequent doses of 1 mg/kg every 3 weeks in combination with gp100 peptide vaccines. To date, 3 of 24 patients (13%) have had objective tumor responses. One of the three responders had a grade 3 adverse event (diarrhea).

A statistically significant correlation was discovered in cohorts 1 and 2 between patients that respond and patients that develop serious adverse events, using both the Chi-square test ($p=0.0146$) and the Fisher's exact test ($p=0.0116$). See Fisher and Van Belle, 1993, Biostatistics: A methodology for the Health Sciences, J. Wiley and Sons, New York.

In another study, seventeen patients with Stage III or IV malignant melanoma were administered a single dose of anti-CTLA-4 antibody 10D1. Two patients had a partial response. There were no serious (grade 3 or 4) adverse events.

Thirteen patients with malignant melanoma were administered anti-CTLA-4 antibody 10D1 (3 mg/kg×2 doses 8 weeks apart) in combination with the approved regimen for MELACINE® (including cyclophosphamide). No objective responses and no serious adverse events were observed. Possible reasons for lack of efficacy include: (1) inhibitory effects of cyclophosphamide, (2) the long dosing interval, and (3) the weak potency of MELACINE® as a vaccine.

In combining the results of the above studies, a statistically significant correlation was discovered between patients who respond and patients who develop serious adverse events, using both the Chi-square test ($p=0.0028$) and the Fisher's exact test ($p=0.0049$).

In a study of nineteen patients with completely resected stage III or IV melanoma, the patients were divided into three cohorts and treated with different doses of anti-CTLA-4 antibody 10D1 (0.1, 1.0 and 3.0 mg/kg monthly for 6 months, then every 3 months×2) in combination with gp100, tyrosinase, and MART-1 vaccines. This study showed dose-dependent induction of organ specific autoimmune-like adverse events, predominately involving skin and gut. The autoimmune-like adverse events were manageable and reversible.

In a study of treatment of chemotherapy-naïve patients with metastatic melanoma, patients were treated with anti-CTLA-4 antibody 10D1 alone or in combination with cytotoxic chemotherapy (dacarbazine). Twenty-four patients enrolled. Four of twelve patients receiving monotherapy and three of twelve patients receiving combination treatment experienced disease progression. One SAE of grade 3 rash and pruritis was observed.

Administration of anti-CTLA-4 antibody has been associated with serious adverse events that are suggestive of autoimmune responses. SAE's were infrequent following a single dose of anti-CTLA-4 antibody given alone at 3 mg/kg. Adverse events occur more often when anti-CTLA-4 antibody is given in multiple doses and in combination with melanoma peptide vaccines. In the study involving administration of anti-CTLA-4 antibody in conjunction with peptide vaccines, reduction in the dose of anti-CTLA-4 antibody in cohort 2 reduced the rate of SAE's. No discernable correlation between plasma concentration of anti-CTLA-4 antibody in an individual patient and the development of SAE's has been found. Statistical analysis of the clinical trial data established an unexpected but highly significant correlation between a BE and therapeutic efficacy. This experimental observation underpins the discovery that dosing anti-CTLA-4 antibody up to the point of inducing a BE (either by the dosage amount, frequency, or both) indicates achievement of a therapeutically maximally effective dose.

Except when noted, the terms "patient" or "subject" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

An "adverse event" (AE) as used herein is any unfavorable and generally unintended, even undesirable, sign (including an abnormal laboratory finding), symptom, or disease associated with the use of a medical treatment or procedure. Most AE's are temporary and reverse upon withdrawal or reduction in dose of the medical treatment, or with treatment of the AE.

The National Cancer Institute defines "adverse event" as any unfavorable and unintended sign (including an abnormal laboratory finding), symptom, or disease temporally associated with the use of a medical treatment or procedure that may or may not be considered related to the medical treatment or procedure (Cancer Therapy Evaluation Program, Common Terminology Criteria for Adverse Events, Version 3.0, DCTD, NCI, NIH, DHHS, Mar. 31, 2003 (http://ctep.cancer.gov), published Apr. 16, 2003 (site visited May 27, 2003)). An "adverse event" is an unintended consequence of treatment. It has been surprisingly discovered that induction of an adverse event is a marker that indicates a sufficient dosage of anti-CTLA-4 antibody has been administered to a patient for the treatment of cancer. In the context of this invention, the "adverse" events are not unintended, but rather are purposely sought because they serve as a surrogate therapeutic endpoint for anti-CTLA-4 based immunotherapy of cancer. Because the signs, symptoms, abnormal laboratory findings and diseases temporally associated with anti-CTLA-4 treatment are an intended consequence of treatment by the methods of the invention, such events are herein referred to as "breakthrough events (BE's)".

A "breakthrough event (BE)" as used herein is an intended sign (including an abnormal laboratory finding), symptom, or disease temporally associated with administration of anti-CTLA-4 antibody that is apart from the therapeutic effect at the tumor site. For example, an autoimmune response that causes dermatitis at a location separate in space from the melanoma under treatment is a BE. A BE is generally an autoimmune event but, for the purposes of the use of the invention in clinical practice, pathological confirmation of an autoimmune etiology is not required; for example, colitis diagnosed clinically of any etiology can be a breakthrough event if the definition is otherwise satisfied. A BE can be graded according to the NCI grading system for adverse events.

An "autoimmune breakthrough event (ABE)" is a breakthrough event that is an autoimmune event. When practicing the present invention preferred breakthrough events are autoimmune breakthrough events. Accordingly, the term "autoimmune breakthrough event" is frequently used to describe the therapeutic methods of this invention. It is understood, however, that the breakthrough events that are useful to such methods need not necessarily be autoimmune events. An autoimmune breakthrough event is a preferred breakthrough event.

A "serious adverse event" (SAE) is a grade 3 or 4 adverse event as defined by the National Cancer Institute (NCI). A grade 3 AE is generally defined as "severe" and a grade 4 AE is generally defined as "life-threatening or disabling". The NCI also specifically defines grade 3 and 4 adverse events. For example, grade 3 colitis consists of abdominal pain, fever, change in bowel habits with ileus, or peritoneal signs (Cancer Therapy Evaluation Program, Common Terminology Criteria for Adverse Events, Version 3.0, DCTD, NCI, NIH, DHHS, Mar. 31, 2003, available at the National Cancer Institute's Cancer Therapy Evaluation Program (CTEP) web site, publication date Apr. 16, 2003. This publication is hereby incorporated by reference.

A "manifestation of non-tumor related autoimmunity" is any clinical event that results from, or appears to result from, immune targeting of antigens on non-cancer cells. Such a BE is particularly indicative of an immunologically mediated therapeutic effect on the cancer cells, since the BE relates to a heightened activation of overall immunity including tumor immunity.

The term "treating" includes the administration of the compounds or agents of the present invention to prevent or delay the onset of the symptoms, complications, or biochemical indicia of a disease, alleviating the symptoms or arresting or inhibiting further development of the disease, condition, or disorder (e.g., autoimmune disease). Treatment may be prophylactic (to prevent or delay the onset of the disease, or to prevent the manifestation of clinical or subclinical symptoms thereof) or therapeutic suppression or alleviation of symptoms after the manifestation of the disease.

The term "advanced cancer" means cancer that is no longer localized to the primary tumor site, or a cancer that is Stage III or IV according to the American Joint Committee on Cancer (AJCC).

The term "therapeutically effective dose" means a dose of anti-CTLA-4 antibody sufficient to induce a cancer to shrink, to slow the progression of a cancer or to stop the progression of a cancer. Alternatively, a "therapeutically effective dose" means a dose of anti-CTLA-4 antibody sufficient to induce a partial or a complete response in a patient with cancer.

The term "lymphocyte" as used herein has the normal meaning in the art, and refers to any of the mononuclear, nonphagocytic leukocytes, found in the blood, lymph, and lymphoid tissues, i.e., B and T lymphocytes.

The terms "cytotoxic T lymphocyte-associated antigen-4," "CTLA-4," "CTLA4," "CTLA-4 antigen" and "CD152" (see, e.g., Murata (1999) Am. J. Pathol. 155:453-460) are used interchangeably, and include variants, isoforms, species homologs of human CTLA-4, and analogs having at least one common epitope with CTLA-4 (see, e.g., Balzano (1992) Int. J. Cancer Suppl. 7:28-32). CTLA-4's complete sequence is found in GenBank Accession No. L15006.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term antibody includes antigen-binding portions of an intact antibody that retain capacity to bind CTLA-4. Examples of binding include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al., Science 1998; 242:423-426; and Huston et al., Proc. Natl. Acad. Sci. USA 1988; 85:5879-5883). Such single chain antibodies are included by reference to the term "antibody" Fragments can be prepared by recombinant techniques or enzymatic or chemical cleavage of intact antibodies.

CTLA-4 antibodies can bind to an epitope on human CTLA-4 so as to inhibit CTLA-4 from interacting with a human B7 counterreceptor. Because interaction of human CTLA-4 with human B7 transduces a signal leading to inactivation of T-cells bearing the human CTLA-4 receptor, antagonism of the interaction effectively induces, augments or prolongs the activation of T cells bearing the human CTLA-4 receptor, thereby prolonging or augmenting an immune response. Anti-CTLA-4 antibodies are described in U.S. Pat. Nos. 5,811,097; 5,855,887; 6,051,227; in PCT Publication Nos. WO 01/14424 and WO 00/37504; and in U.S. Publication No. 2002/0039581 A1. Each of these references is specifically incorporated herein by reference for purposes of description of anti-CTLA-4 antibodies. A preferred clinical anti-CTLA-4 antibody is human monoclonal antibody 10D1 (MDX010) as disclosed in WO 01/14424.

The phrase "immune cell response" refers to the response of immune system cells to external or internal stimuli (e.g., antigen, cytokines, chemokines, and other cells) producing biochemical changes in the immune cells that result in immune cell migration, killing of target cells, phagocytosis, production of antibodies, other soluble effectors of the immune response, and the like.

The terms "T lymphocyte response" and "T lymphocyte activity" are used here interchangeably to refer to the component of immune response dependent on T lymphocytes (i.e., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

The term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

As used herein, the phrase "cell surface receptor" includes molecules and complexes of molecules capable of receiving a signal and the transmission of such a signal across the plasma membrane of a cell. An example of a "cell surface receptor" of the present invention is the T cell receptor (TCR) or the B7 ligands of CTLA-4.

The term "nonspecific T cell activation" refers to the stimulation of T cells independent of their antigenic specificity.

"Target cell" shall mean any undesirable cell in a subject (e.g., a human or animal) that can be targeted by a composition (e.g., a human sequence antibody or a human monoclonal antibody of the invention, a bispecific or a multispecific molecule of the invention). The target cell can be a cell expressing or overexpressing human CTLA-4. Cells expressing human CTLA-4 can include tumor cells, e.g. lymphomas.

Also included in the invention are modified antibodies. The term "modified antibody" includes antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody.

The antibody conjugates of the invention can be used to modify a given biological response or create a biological response (e.g., to recruit effector cells). The drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-alpha; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Inducement of a Breakthrough Event

The objective of the present method is to achieve the BE in the shortest amount of time while avoiding overdosage. This is accomplished by titrating the dosage of medication to induce the BE. Methods of titrating medication dosage to achieve a desired effect are well-known in the medical art as, for example, in the treatment of hypertension in which the dosage of anti-hypertensive medication is titrated to achieve the desired effect on blood pressure. Such methods include, for example, repeating the same dosage amount of a medication at a fixed dosage interval, but more preferably increasing the dosage amount, decreasing the dosage interval, or a combination of altering dosage amount and dosage interval.

An initial dose of anti-CTLA-4 antibody typically comprises 3 to 10 mg/kg antibody administered every 3 to 8 weeks. Following an initial dose of anti-CTLA-4 antibody, a patient is monitored by a clinician for a sufficient period of time, which is typically over the course of the dosage interval or 1 to 4 weeks, to detect a BE (see below for methods of detection). Since a BE may require expansion of autoreactive T-cells, it is expected that this event could take 1-4 weeks to manifest after any therapeutically effective dose. The absence of a BE during the monitoring period is an indication to the clinician that further administration of anti-CTLA-4 antibody is required. Following a dose of anti-CTLA-4 antibody, the patient is monitored for a BE, and additional dosages are administered until, at least, a BE is induced and detected. It shall be appreciated by those of skill in the art that factors, including the patient's immune state, which may be affected by prior immune therapies, disease state, age, etc., can impact the dosage required to elicit a BE. A skilled clinician will be able to take such factors into account when determining the initial dose, as well as any subsequent doses, to induce a BE. These factors should be considered in determining the initial dose, as well as subsequent dosages, to induce a BE.

Since a method of the invention is to induce a BE in the shortest period of time without causing an overdose in the patient, it is advantageous to shorten the period for monitoring the patient for a BE to 1 to 4 weeks, more preferably 2 to 3 weeks. If an additional dose is required to achieve a BE, the dosage can be increased by, e.g., 10 to 100% of the prior dosage. For example, if the patient initially receives 3 mg/kg and is scheduled to receive a second dose 3 weeks later, but does not achieve a BE after the 3 week period, then the patient's dosage can be increased to 6 mg/kg (i.e., 100% increase). In another example, if the patient initially receives 10 mg/kg and is scheduled to receive a second dose 8 weeks later, but does not achieve a BE after monitoring for 4 weeks, then the patient's dosage interval can be reduced from 8 weeks to 4 weeks, while maintaining the 10 mg/kg dosage. One skilled in the art shall appreciate that various dosage amount and interval changes can be made in practicing a method of the invention to induce a BE.

Detecting a Breakthrough Event

A BE can manifest as a symptom, sign, or laboratory abnormality. Accordingly, detection of such an event requires a patient history (for subjective complaints), a physical examination and/or imaging studies (for objective signs), and laboratory studies (for laboratory abnormalities). Depending on the initial findings, a clinician may elect to order additional studies such as, for example, an endoscopy or a biopsy.

A clinician is particularly vigilant regarding detection of more common BE's such as, for example, those involving the skin (dermatitis, rash, pruritis), gastrointestinal tract (abdominal pain, tenderness, diarrhea), endocrine system (suppression of hormone levels), and liver (hepatitis, elevation of liver function tests). The clinician, however, must be prepared to detect any BE. The Cancer Therapy Evaluation Program, Common Terminology Criteria for Adverse Events lists BE's (adverse events) and provides a grading system for these events. This publication can also serve as a guide to aid the clinician in the monitoring patients and detecting BE's.

Patient monitoring includes periodic comprehensive histories for subjective complaints and comprehensive physical examination. Each organ system susceptible to a BE is examined. For example, the history related to the dermatologic system includes questions regarding itching, scaling, pain, and changes in skin color. The physical examination of the skin includes, for example, close inspection of all the visible dermis. Further studies, based on the judgment of the clinician, can include, for example, skin biopsy.

BE's in organ systems that are not readily amenable to physical examination, and that are asymptomatic, require added reliance on laboratory studies and imaging studies. For example, hepatitis may be detected at earlier stage using liver function tests and CT scan than by physical examination.

The detection of BE's is dependent on clinical monitoring of patients following administration of anti-CTLA-4 antibody. A broad array of diagnostic methods may be used by the clinician to detect a BE.

Cancer Treatment

The CTLA-4 antibodies of the invention and surrogate therapeutic endpoint can be used in the treatment of malignancies, where the patient has previously received a cancer vaccine or demonstrates some level of natural protective immunity to the tumor. The antibodies can be used as a single agent or in combination with one or more other therapeutic agents or in conjunction with an immunotherapeutic vaccine for the tumor, such as chemotherapy, radiation therapy, cytokines, chemokines and other biologic signaling molecules, tumor specific vaccines, autologous and allogeneic stem cell rescue (e.g., to augment graft versus tumor effects), other therapeutic antibodies, molecular targeted therapies, anti-angiogenic therapy, infectious agents with therapeutic intent (such as tumor localizing bacteria), and gene therapy. The antibodies can be administered as a single dose or as multiple doses. The antibodies can be used in adjuvant or neoadjuvant therapy, either alone or in conjunction with the aforementioned therapies.

A therapeutic agent, which is intended to treat the BE, e.g., steroids can also be used in a method of the invention. Thus, a therapeutic agent that treats the BE is administered to the patient following diagnosis of the BE.

The present invention is directed to the treatment of tumors, particularly immunologically sensitive tumors, which are cancers that respond to immunotherapy or cancers that manifest in patients who are immunocompromised. In one embodiment the tumor is a solid tumor. Examples of tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, lymphoma, melanoma, Kaposi's sarcoma, Ewing's tumor, leiomyosarcoma, rhabdomyosarcoma, colo-rectal carcinoma, gastric carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In another embodiment, dysproliferative changes (such as metaplasias and dysplasias) are treated or prevented in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68-79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, *Medicine*, 2d Ed., J. B. Lippincott Co., Philadelphia.

The present invention is also directed to treatment of non-malignant tumors and other disorders involving inappropriate cell or tissue growth augmented by angiogenesis by administering a therapeutically effective amount of a vector of the invention to the tissue undergoing inappropriate growth. For example, it is contemplated that the invention is useful for the treatment of arteriovenous (AV) malformations, particularly in intracranial sites. The invention may also be used to treat psoriasis, a dermatologic condition that is characterized by inflammation and vascular proliferation; and benign prostatic hypertrophy, a condition associated with inflammation and possibly vascular proliferation. Treatment of other hyperproliferative disorders is also contemplate Treatment with an anti-CTLA-4 antibody can be used to activate a pre-existing memory response in patients treated with a cancer vaccine. Thus, vaccine-treated patients can be selected for further treatment with an anti-CTLA-4 antibody to thereby further induce or enhance an immune response.

In one embodiment, the patient has been previously treated with an anti-cancer vaccine. The cancer antigen can be, for example, a melanoma antigen or a prostate cancer antigen. In one embodiment, the patient is a human. In a preferred embodiment, the anti-CTLA-4 antibody is a human anti-CTLA-4 antibody. A preferred human anti-CTLA-4 antibody of the invention is 10D 1, but the methods of the present invention can be used with any human CTLA-4 antibody. In other embodiments, the anti-CTLA-4 antibody is a recombinant antibody such as a chimeric or humanized (e.g., CDR-grafted) anti-CTLA-4 antibody.

Blockade of CTLA-4 by antibodies can enhance the memory or secondary immune response to cancerous cells in the patient. Antibodies to CTLA-4 can be combined with an immunogenic agent, such as cancerous cells, purified tumor antigens (including recombinant proteins, peptides, and carbohydrate molecules), cells, and cells transfected with genes encoding immune stimulating cytokines and cell surface antigens such as B7 (see, e.g., Hurwitz, A. et al. (1998) Proc. Natl. Acad. Sci U.S.A. 1998; 95:10067-10071), or used alone, to stimulate immunity.

CTLA-4 blockade is effective when following a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, *Cancer: Principles and Practice of Oncology*, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. Proc. Natl. Acad. Sci U.S.A. 1993; 90: 3539-43).

Anti-CTLA-4 blockade to boost GMCSF-modified tumor cell vaccines improves efficacy of vaccines in a number of experimental tumor models such as mammary carcinoma (Hurwitz et al., 1998, supra), primary prostate cancer (Hurwitz et al., Cancer Research 2000; 60:2444-8) and melanoma (van Elsas et al. J. Exp. Med. 1999, 190:355-66). In these instances, non-immunogenic tumors, such as the B16 melanoma, have been rendered susceptible to destruction by the immune system. The tumor cell vaccine may also be modified to express other immune activators such as IL2, and costimulatory molecules, among others.

The study of gene expression and large scale gene expression patterns in various tumors has led to the definition of so called "tumor specific antigens" (Rosenberg, Immunity 1999; 10:281-7). In many cases, these tumor specific antigens are differentiation antigens expressed in the tumors and in the cell from which the tumor arose, for example melanocyte antigens gp100, MAGE antigens, Trp-2. More importantly, many of these antigens can be shown to be the targets of tumor specific T cells found in the host. CTLA-4 blockade may be used as a boosting agent in conjunction with vaccines based on recombinant versions of proteins and/or peptides found to be expressed in a tumor in order to potentiate a secondary or memory immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim et al., Science 1994; 266:2011-2013). These somatic tissues may be protected from immune attack by various means. Tumor antigen may also be "neo-antigens" expressed in cancer cells because of somatic mutations that alter protein sequence or create fusion proteins between two unrelated sequences (i.e. bcr-abl in the Philadelphia chromosome), or idiotype from B cell tumors. Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with CTLA-4 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot and Srivastava, Science 1995; 269:1585-1588; Tamura et al., Science 1997, 278: 117-120.

Dendritic cells (DC) are potent antigen presenting cells that can be used to prime antigen-specific responses. DC's can be produced ex vivo and loaded with various protein and peptide antigens as well as tumor cell extracts (Nestle et al., Nature Medicine 1998; 4:328-332). DCs may also be transduced by genetic means to express these tumor antigens as well. DCs have also been fused directly to tumor cells for the purposes of immunization (Kugler et al., Nature Medicine 2000; 6:332-336). As a method of vaccination, DC immunization may be effectively boosted with CTLA-4 blockade to activate more potent anti-tumor responses.

Another type of melanoma vaccine that can be combined with CTLA-4 blockade is a vaccine prepared from a melanoma cell line lysate, in conjunction with an immunological adjuvant, such as the MELACINE® vaccine, a mixture of lysates from two human melanoma cell lines plus DETOX™ immunological adjuvant. Vaccine treatment can be boosted with anti-CTLA4, with or without additional chemotherapeutic treatment.

Infectious Diseases

Other methods of the invention are used to treat patients that have been exposed to particular toxins or pathogens. Similar to its application to tumors as discussed above, antibody mediated CTLA-4 blockade and surrogate therapeutic endpoint can be used alone, or as an adjuvant, in combination with vaccines, to stimulate the secondary or memory immune response to pathogens, toxins, and self-antigens. CTLA-4 blockade has been shown to be effective in the acute phase of infections of *Nippostrongylus brasiliensis* (McCoy, K. et al. (1997) 186(2); 183-187) and *Leishmania donovani* (Murphy, M. et al. (1998) J. Immunol. 161:4153-4160). Examples of pathogens for which this therapeutic approach may be particularly useful include pathogens for which there is currently no effective vaccine, or pathogens for which conventional vaccines are less than completely effective. These include, but are not limited to HIV, Hepatitis (A, B, & C), Influenza, Herpes, Giardia, Malaria, Leishmania, *Staphylococcus aureus*, and *Pseudomonas aeruginosa*. CTLA-4 blockade is particularly useful in boosting immunity against established infections by agents such as HIV that present altered antigens over the course of the infections. These novel epitopes are recognized as foreign at the time of anti-human CTLA-4 administration, thus provoking a strong T cell response that is not dampened by negative signals through CTLA-4.

Some examples of pathogenic viruses causing infections treatable by methods of the invention include hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include *chlamydia, rickettsial bacteria, mycobacteria, staphylococci, streptococci, pneumonococci, meningococci* and *conococci, klebsiella, proteus, serratia, pseudomonas, legionella, diphtheria, salmonella, bacilli, cholera, tetanus, botulism, anthrax, plague, leptospirosis*, and Lyme disease bacteria.

Some examples of pathogenic fungi causing infections treatable by methods of the invention include *Candida (albicans, krusei, glabrata, tropicalis,* etc.), *Cryptococcus neoformans, Aspergillus (fumigatus, niger,* etc.), *Genus Mucorales (Mucor, Absidia, Rhizophus), Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

Promoting Beneficial Autoimmune Reactions

The ability of anti-CTLA-4 antibodies and surrogate therapeutic endpoint to provoke and amplify autoimmune responses has been documented in a number of experimental systems (EAE—Experimental Autoimmune Encephalomyelitis, a murine model for MS (Perrin et al., J Immunol 1996; 157:1333-1336); diabetes (Luhder et al., 1998, supra). Indeed, induction of anti-tumor responses using tumor cell and peptide vaccines reveals that many anti-tumor responses involve anti-self reactivities (depigmentation observed in anti-CTLA-4+GM-CSF modified B16 melanoma in van Elsas et al. supra; depigmentation in Trp-2 vaccinated mice (Overwijk et al., Proc. Natl. Acad. Sci. U.S.A. 1999 96:2982-2987); autoimmune prostatitis evoked by TRAMP tumor cell vaccines (Hurwitz 2000, supra), melanoma peptide antigen vaccination and vitiligo observed in human clinical trials (Rosenberg and White, J Immunother Emphasis Tumor Immunol 1996; 19: 81-4).

Therefore, it is possible to consider using anti-CTLA-4 boosting in conjunction with various self-proteins in order to devise vaccination protocols to efficiently generate immune responses against these self-proteins for disease treatment. For example, Alzheimer's disease involves inappropriate accumulation of Aβ peptide in amyloid deposits in the brain; antibody responses against amyloid are able to clear these amyloid deposits (Schenk et al., Nature 1999; 400:173-177).

Other self-proteins may also be used as targets such as IgE for the treatment of allergy and asthma, and TNF for rheumatoid arthritis. Finally, antibody responses to various hormones may be induced by the use of anti-CTLA-4 antibody. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-CTLA-4 antibody and surrogate therapeutic endpoint can be used for induction of therapeutic autoimmune responses to treat patients having an inappropriate accumulation of other self-antigens, such as amyloid deposits, including Aβ in Alzheimer's disease, cytokines such as TNFα, and IgE.

EXAMPLES

The present invention is also described by means of the following examples. However, the use of these or other examples anywhere in the specification is illustrative only and in no way limits the scope and meaning of the invention or of any exemplified term. Likewise, the invention is not limited to any particular preferred embodiments described herein. Indeed, many modifications and variations of the invention may be apparent to those skilled in the art upon reading this specification and can be made without departing from its spirit and scope. The invention is therefore to be limited only by the terms of the appended claims along with the full scope of equivalents to which the claims are entitled.

Example 1

Results from a Clinical Trial of Anti-CTLA-4 Antibody with Melanoma Peptides/IFA for Resected Stages III/IV Melanoma Nineteen patients with resected Stage III (2 patients) or IV (17 patients) melanoma received doses (0.3, 1 and 3 mg/kg)

of CTLA-4 antibody 10D1 with each injection of gp100/tyrosinase/MART-1 peptide vaccine with incomplete Freund's adjuvant (IFA). The patients were HLA-A2$^+$ and had no prior treatment with IFN-α. The tumors were IHC positive for gp100, tyrosinase and/or MART-1. Exclusion criteria included autoimmune disease and prior treatment with MDX-010, or MART-1, gp100 and tyrosinase peptides. The tyrosinase 368-376 (370D), MART-1 26-35 (27L) and gp100 209-217 (210M) peptides each differed from wild type by one amino acid modification to increase HLA binding.

Anti-CTLA-4 antibody and the peptide vaccines were administered every 4 weeks for 6 weeks, then every 3 months×2 (8 doses total). The peptide vaccines were administered subcutaneously at 1 mg each per dose emulsified in IFA. Three cohorts received 0.3, 1.0, or 3.0 mg/kg IV of anti-CTLA-4 antibody.

TABLE 1

Disease Status and Drug Related Serious Adverse Events

| Dosing cohort | Patient | Sex/Age | Prior Treatment (I = immunotherapy, C = chemotherapy, R = radiotherapy) | SAE's | Disease status |
|---|---|---|---|---|---|
| 0.3 mg/kg | 1 | M/43 | I, C | None | |
| | 2 | F/40 | I, C | None | Relapsed |
| | 3 | F/69 | I, C | None | |
| | 4 | F/22 | I, C | None | |
| | 5 | M/57 | I, C | None | Relapsed |
| | 6 | F/54 | None | None | Relapsed |
| | 7 | F/41 | R, I | None | |
| 1.0 mg/kg | 8 | M/58 | None | None | Relapsed |
| | 9 | F/69 | R | None | |
| | 10 | M/64 | None | None | Relapsed |
| | 11 | F/43 | I | None | Relapsed |
| | 12 | M/48 | I | None | |
| | 13 | F/59 | None | None | |
| | 19 | M/56 | None | Grade 3 diarrhea, grade 3 fever, grade 3 bloody stool, bilateral uveitis | |
| 3.0 mg/kg | 14 | M/36 | None | None | |
| | 15 | F/42 | I, C | Grade 3 diarrhea | |
| | 16 | M/40 | I | | |
| | 17 | M/54 | I | None | |
| | 18 | M/41 | None | Grade 3 diarrhea Grade 3 abdominal pain, grade 2 diarrhea | |

TABLE 2

Dosing Summary

| Dose | | Number of doses | | | | | | | Average doses per patient | Status | | |
|---|---|---|---|---|---|---|---|---|---|---|---|---|
| mg/kg | n | 1 | 2 | 3 | 4 | 5 | 6 | 7 | | Lost to follow-up | Tox | PD |
| 0.3 | 7 | | | 1 | | 4 | 2 | | 5.8 | 4 | | 3 |
| 1.0 | 7 | 1 | 1 | 1 | 1 | 1 | 2 | | 4.3 | | 1* | 3 |
| 3.0 | 5 | 1 | 1 | 1 | | 1 | | 1 | 4.0 | | 3* | |

*MDX-010 discontinued due to autoimmune manifestations, peptides continued

SAE's included:

1) A 40 year old male developed grade 2 diarrhea (two days) and grade 3 abdominal pain (ten days) after the first infusion of 3 mg/kg of anti-CTLA-4 antibody. CT scan of the abdomen and pelvis showed thickening and inflammation of the terminal ileum and cecal wall. A repeat CT scan four days later showed resolution of the abnormal findings. The patient was treated for his symptoms, which resolved 16 days from onset.

2) A 42 year old female developed grade 3 diarrhea six days after the second infusion of 3 mg/kg of anti-CTLA-4 antibody. The patient was treated with IV hydration and antibiotics.

3) A 54 year old male developed grade 3 diarrhea after the third infusion of 3 mg/kg of anti-CTLA-4 antibody. The patient's stool was positive for white blood cells (WBC). The diarrhea was treated with antibiotics and resolved 8 days after onset.

4) A 56 year old male developed grade 3 bloody diarrhea and bilateral uveitis after the second infusion of 1 mg/kg of anti-CTLA-4 antibody. The patient's stool was positive for WBC, sigmoidoscopy revealed inflamed bowel wall, and CT scan showed a thickened cecal wall. The patient had an almost immediate response to treatment with oral and topical steroids. All symptoms resolved after three months.

Conclusions

There were no relapses in the highest dose cohort. Anti-CTLA-4 antibody dose-dependent, organ-specific auto-immune-like adverse events were observed. These adverse events were manageable and reversible.

Example 2

Results from a Clinical Trial of Single-dose Anti-CTLA4 Antibody in Patients with Surgically Unresectable Stage III or IV Melanoma A Phase I open-label, multicenter clinical trial was conducted to evaluate the safety and pharmacokinetics of MAb 10D1 in seventeen patients with progressive, unresectable, malignant melanoma. Median age was 59 years (range 29-79). Nine patients had received prior immunotherapy, six had prior radiation and five had prior chemotherapy. All patients received a single dose of 3 mg/kg of 10D1 intravenously over 90 minutes and were then followed for toxicity, pharmacokinetics, circulating T cell activation and clinical outcome. All infusions were completed with only mild adverse events. Seven patients had mild, reversible rashes or pruritis. Plasma levels of antibody persisted from one to four months. There was no significant increase in activated peripheral T cells and no evidence of clinical autoimmunity beyond the mild rash. Two patients experienced a partial response including resolution of three soft tissue masses and over 50% reduction of a lung mass. Furthermore, the patient experiencing the over 50% reduction in lung mass was a patient who previously had been treated with a melanoma vaccine, suggesting that the anti-CTLA-4 antibody treatment was capable of activating a pre-existing memory response to the tumor. The results of this study indicate that anti-CTLA-4 treatment was well tolerated with clear evidence of immunologic and anti-tumor activity.

TABLE 2

Summary of patient characteristics and results

| Patient | Sex | Age (yrs) | Prior Treatment[1] | Best Response Status and Duration[2] | Metastatic Disease Sites | Areas of Response | Serious Adverse Events |
|---|---|---|---|---|---|---|---|
| 1 | F | 66 | R, C | SD | Lung, liver | | |
| 2 | F | 69 | None | PD | Liver | | |
| 3 | M | 43 | C, I | SD | Lymph node | | |
| 4 | M | 56 | R, C, I | PD | Lymph node, bone, peri-anal | | |
| 5 | M | 43 | R, C, I | PD | Spleen, adrenal, CNS, lung, retroperitoneum, skin | | |
| 6 | M | 58 | R, I | SD | Lung, lymph node, CNS | | |
| 7 | M | 49 | I | PD | Skin, lung, liver, lymph node | | |
| 8 | F | 70 | H | PD | Lung, skin, liver | | |
| 9 | F | 79 | None | PD | Unknown | | |
| 10 | M | 74 | R, C | PD | Lymph node, lung, pancreas, kidney | | Grade III atrial fibrillation |
| 11 | M | 76 | None | PR, 7 months | Lymph node, skin, lung, abdomen | Lymph node, skin, lung, abdomen | |
| 12 | F | 49 | I[1] | PR, 9 months | Lung, skin, pleural effusion | Lung, skin, pleural effusion | |
| 13 | M | 52 | C, I | PD | Lung, liver | | |
| 14 | M | 61 | C, I | PD | Lung | | |
| 15 | M | 29 | R, C | SD | Lymph node, lung | | |
| 16 | M | 70 | None | PD | Skin, liver, spleen | | |
| 17 | F | 63 | None | PD | Lung, lymph node | | |

[1]H = hormonal, R = radiotherapy, C = chemotherapy, I = immunotherapy
[2]PD = progressive disease, PR = partial response, SD = stable disease
[1]Immunotherapy included IL-2 and dendritic cell vaccine.

Example 3

Results from a Clinical Trial of Anti-CTLA-4 Antibody in Combination with gp100 Peptide Vaccines A. Cohort 1

Fourteen patients with progressive Stage IV melanoma received anti-CTLA-4 antibody 10D1 in conjunction with vaccination with two HLA-A*0201-restricted gp100 peptides. Patient characteristics are summarized in Table 3.

fied in incomplete Freund's adjuvant (IFA) injected subcutaneously in one extremity and 1 mg of gp100:280-288(288V) peptide (YLEPGPVTV) emulsified in IFA injected subcutaneously in a second extremity (synthetic peptides provided by the National Cancer Institute Cancer Therapy Evaluation Program). Patients underwent apheresis prior to treatment and three weeks following every two treatment cycles. Peripheral blood mononuclear cells (PBMC) were isolated by Ficoll-Hypaque separation and cryopreserved in heat-inactivated human AB serum with 10% dimethyl sulphoxide and stored at −180° C. until further use.

TABLE 3

Patient characteristics and results

| Patient | Age/Sex | Metastatic Disease Sites | Prior Therapy[1] | Best Response[2] and Duration | Areas of Response | SAE's |
|---|---|---|---|---|---|---|
| 1 | 52/M | Lung | C, I | PR (8+ months, continuing) | Lung | Grade 3 pruritis, Grade 3 diarrhea |
| 2 | 40/F | Lymph node | H, C, I | SD | | Grade 3 rash/desquamation |
| 3 | 39/M | Skin, lymph node, lung | None | SD | | |
| 4 | 55/F | Skin | I | SD | | |
| 5 | 67/M | Bone, liver, lung, lymph node, skin, intramuscular | C, I, R | PD | | |
| 6 | 58/M | Lung, skin | I | PD | | |
| 7 | 48/M | CNS[3], lung | I | PD | | |
| 8 | 48/M | Lung, liver, adrenal, lymph node, skin | C, I | PD | | |
| 9 | 52/M | Lymph node | I | SD | | Grade 3 diarrhea |
| 10 | 62/M | Lung, lymph node | C, I | SD | | |
| 11 | 54/M | Lung, CNS, skin | None | CR (7+ months, continuing)[4] | Lung, CNS, skin | Grade 3 hypopituitary/confusion |
| 12 | 43/M | Intraperitoneal, intramuscular, skin | I | SD | | Grade 4 LFT elevation[5] |
| 13 | 49/F | Lung, adrenal | C, I | CR (7+ months, continuing) | Lung, adrenal | Grade 3 rash/desquamation |
| 14 | 63/M | Lung, pelvis, lymph node | None | SD | | |

[1] C = chemotherapy, H = hormonal, I = immunotherapy, R = radiotherapy
[2] PD = progressive disease, SD = stable disease, PR = partial response, CR = complete response.
[3] CNS = central nervous system
[4] The patient's condition appeared to worsen prior to showing a positive response
[5] LFT = liver function test All patients were HLA*0201+ with a Karnofsky performance status ≧60%. Six patients had visceral metastases. The patients had no evidence of autoimmune or immunodeficiency disease. All patients had prior surgery for their primary lesion. Six patients had prior chemotherapy. Eleven patients had prior immunotherapy including interferon-α (Patients 2, 5-8, 10, 12 and 13), low-dose IL-2 (Patients 2, 5 and 13), high-dose intravenous IL-2 (Patients 4, 7 and 8), whole cell melanoma vaccines (Patients 1, 2 and 6), NY-ESO-1 peptide vaccine (Patients 4 and 5), and GM-CSF (Patient 9). The patients had no prior gp100 immunization and had no systemic therapy in the three weeks prior to treatment.

A treatment cycle was administered every three weeks, which consisted of anti-CTLA-4 antibody 10D1 at 3 mg/kg administered intravenously over 90 minutes followed by 1 mg of gp100:209-217(210M) peptide (IMDQVPFSV) emulsi- Clinical response was evaluated using computed axial tomography (CT) of the chest, abdomen and pelvis; and magnetic resonance imaging (MRI) of the brain. These imaging studies were performed within 4 weeks of starting treatment and then after every two treatment cycles. Additional radiological studies were used as needed to evaluate disease sites. The sum of the longest diameters of the tumors in each patient (World Health Organization RECIST criteria) was calculated before and after treatment. A partial response was defined as a decrease of at least 30%, but less than 100%, in the sum of the longest diameters of all evaluable metastases lasting at least one month, and no new or enlarging tumors. A complete response was defined as a decrease of 100% in the sum of the longest diameters of all evaluable metastases lasting at least one month, and no new tumors.

Patients were evaluated for autoimmune responses. Patients received an ophthalmologic examination prior to treatment and three months following initiation treatment. All patients had negative serum blood tests prior to initiation of the study for thyroglobulin Ab, rheumatoid factor and anti-nuclear antibody. Human anti-human (anti-idiotypic) Ab, erythrocyte sedimentation rate, anti-nuclear Ab, thyroid stimulating hormone and free T4 levels were measured every three weeks during the study.

Plasma concentrations of MDX-010 were determined using standard ELISA with microtiter wells coated with CTLA-4-Ig (R&D Systems, Minneapolis, Minnesota). Dilutions of plasma samples were incubated on the plates. Bound anti-CTLA-4 Ab was detected with alkaline phosphatase-labeled goat anti-human IgG F(ab)-specific probe, which was developed with p-NPP substrate.

A twelve-day in vitro sensitization assay, which is more sensitive than ELISPOT or tetramer assays, was used to assess immunologic reactivity in all eleven patients with PBMC available for testing. (Rosenberg, S. A. et al., Immunologic and therapeutic evaluation of a synthetic peptide vaccine for the treatment of patients with metastatic melanoma. Nat. Med. 4:321-327 (1998)) Cryopreserved PBMC were thawed and cultured in complete Iscove's-based media with 10% heat-inactivated human AB serum with 1 μM of native gp100:209-217 or gp100:280-288 peptide and 300 IU/ml IL-2. Cells were harvested 11 to 13 days after initiation of the culture and co-incubated with tumor cells or peptide-pulsed T2 cells overnight. Interferon-γ (IFN-γ) release in the supernatant was measured using commercial ELISA assays (Pierce-Endogen, Rockford, Ill.). All eleven patients exhibited successful immunization against the native gp100:209-217 peptide after one to four treatment cycles. Six patients were successfully immunized against the native gp100:280-288 peptide.

Flow cytometry analyses were performed after Fc-receptor blocking and staining with antibodies (BD Biosciences, San Diego, Calif.) or tetramers (Beckman Coulter Immunomics, San Diego, Calif.). Surface marker expression on PBMC of nine patients before and after two cycles of treatment was compared. HLA-DR (an activation marker) expression was significantly increased on post-therapy $CD3^+CD4^+$ cells (P=0.0004; paired t-test) and $CD3^+CD4^+$ (presumably $CD8^+$) cells (P=0.04). $CD3^+CD4^+$ cells also showed significantly increased expression of CD45RO (a memory cell marker) post-therapy (P=0.04). The percent of cell populations expressing CD69, CD25 and CTLA-4 did not change.

Patients 1, 11 and 13 were responders. (Table 15) Patient 1 had shrinkage of a solitary lung lesion after two treatment cycles. Patient 13 had complete resolution of a solitary lung lesion and an adrenal lesion. Patient 11 had 31 lung lesions, two subcutaneous lesions and one brain lesion. The brain lesion grew from 0.5 cm to approximately 1.0 cm after two treatment cycles. Following three additional treatment cycles, Patient 11 had complete resolution of all lesions, including the brain lesion.

Grade 1/2 adverse events included diarrhea (Patients 3, 5 and 14), skin rash (Patient 14), pulmonary infiltrates and mild pleuritic chest pain (Patient 4) and vitiligo (Patients 2 and 6).

Six patients developed seven Grade 3 adverse events including dermatitis (Patients 1, 2 and 13), colitis/entercolitis (Patients 1 and 9), hypophysitis (inflammation of the pituitary gland) (Patient 11), and hepatitis (Patient 12). All patients recovered following discontinuation of treatment and the administration of supportive care and/or steroid therapy. There were no relapses or subsequent autoimmune events.

Autoimmune screening blood tests were normal except for Patients 5 and 12 who developed anti-nuclear antibody (ANA).

The mean peak of MDX-010 after the first dose was 72±33 μg/mL and the trough before the second dose was 12±7 μg/mL. No clear correlation between plasma concentrations or antibody clearance and tumor regression or toxicity was observed.

Patient 1, a partial responder, developed a generalized erythematous maculopapular rash associated with severe pruritis one week after the second treatment cycle. A skin biopsy showed perivascular lymphocytic and eosinophilic infiltrate, papillary dermal edema and epidermal spongiosis consistent with an allergic drug eruption. Two days later, Patient 1 developed severe diarrhea and he was given IV hydration. Gastrointestinal endoscopy and biopsy showed multiple areas of inflammation and mucosal ulceration with marked duodenal and colonic lymphocytosis, plasmacytosis and eosinophilia. Immunohistochemical studies indicated a predominance of $CD3^+$ cells ($CD8^+>CD4^+$ cells) in the inflammatory infiltrate, polyclonality of the plasma cells and increased MHC-1 and HLA-DR expression in the vasculature and epithelium. Autoimmune enterocolitis was diagnosed and the patient was treated with IV methylprednisolone. The patient had marked clinical improvement within 24 hours and the steroids were tapered over five days. The patient had no relapse of symptoms.

Patient 2 developed mild generalized pruritis one week after the first cycle of treatment, which progressed over the following two weeks to severe, circumferential, erythematous macular rash on the extremities where she had received the vaccine injections (right arm and left leg). Skin biopsy showed epidermal spongiosis, significant papillary dermal edema, and a prominent lymphocytic and eosinophilic infiltrate with vascular involvement as seen in collagen autoimmunity. Patient 2 was treated symptomatically with hydroxyzine and diphenhydramine. The rash cleared after several weeks. The patient developed vitiligo on both upper extremities over the following three weeks.

Patient 9 developed diarrhea 11 days after the second cycle of treatment. Endoscopy showed pan-colitis. Colonic biopsy showed severe inflammation with marked cellular infiltration and crypt abscesses. Immunohistochemical studies demonstrated that the majority of infiltrating lymphocytes were $CD3^+$ (with a predominance of $CD4^+$ cells), the plasma cells were polyclonal and epithelial MHC-1 and HLA-DR expression were increased. The patient's diarrhea improved with IV methylprednisolone treatment and was controlled with a slow taper of oral dexamethasone.

Patient 11, a complete responder, developed personality changes and memory problems after receiving the fourth treatment cycle. MRI of the brain showed disappearance of a left temporal metastasis and no other abnormalities. Further evaluation showed undetectable levels of thyroid stimulating hormone, free T4, adrenocorticotropic hormone, growth hormone, prolactin and testosterone suggestive of pan-hypopituitarism. A repeat, focused MRI showed the pituitary gland to be at the upper size limit of normal. High dose steroids were not used because the patient had a complete clinical response. The patient received replacement doses of thyroxine, testosterone and hydrocortisone. The patient's personality and memory abnormalities resolved. A follow-up MRI six weeks later showed a slight decrease in the size of the pituitary gland.

Patient 12 developed abnormal liver enzymes and anti-nuclear antibodies on routine blood tests done three weeks after the third cycle of treatment. Liver biopsy showed acute hepatitis with numerous foci of lobular inflammation consisting mainly of lymphocytes. Immunohistochemical studies revealed a predominately $CD3^+$ cellular infiltrate with $CD4^+$ cells mainly in the peri-portal areas and CD8+ cells mainly in the hepatic lobules. Over the following two weeks, the patient's alanine aminotransferase levels peaked at 2860 U/L (normal is 6-41) and aspartate aminotransferase levels peaked at 1193 U/L (normal is 9-34). Low dose oral prednisone therapy was instituted and all values decreased to normal over the following four months.

Patient 13, a partial responder, developed a severe generalized erythematous and pruritic rash one week after receiving the fourth cycle of treatment. Skin biopsy showed a perivascular lymphocytic infiltration with abundant eosinophils in the superficial dermis. Immunohistochemical studies revealed mainly CD3+ cells (CD4+>CD8+ cells). Lymphocytes cultured from a biopsy of the rash were all CD8+ and 97% reacted with gp100:209-217:HLA-A*0201 tetramer. The rash slowly resolved with hydroxyzine treatment.

B. Cohort 2

The protocol of cohort 2 was the same as cohort 1 except that following an initial loading dose of 3 mg/kg of anti-CTLA-4 antibody, the patients in cohort 2 received doses of 1 mg/kg of anti-CTLA-4 antibody every three weeks in combination with the peptide vaccines. The cohort 2 study is on-going. To date, three of 24 patients (13%) have had an objective tumor response and two of 24 patients have had SAE's (8%).

TABLE 4

Summary of patient characteristics and results

| Patient | Sex | Age | Prior Treatment[1] | Best Response Status and Duration[2] | Metastatic Disease Sites | Areas of Response | SAE's |
|---|---|---|---|---|---|---|---|
| 15 | F | 54 | C | PR (2+ months) | Lung, lymph node | Lung, Lymph node | Grade 3 diarrhea |
| 16 | M | 39 | R, I | PD | Lymph node, liver, lung, skin | | |
| 17 | M | 48 | None | PD | Adrenal, CNS, lung, lymph node, skin | | Grade 3 diarrhea |
| 18 | M | 32 | R, C, I | PD | Liver, lung, lymph node | | |
| 19 | F | 60 | None | PR (2+ months) | CNS, gallbladder, lung, lymph node, skin | CNS, gallbladder, lung, lymph node, skin | |
| 20 | M | 62 | I | Not available (N/A)[3] | Adrenal, bone, lymph node, spleen | | |
| 21 | M | 50 | None | N/A | Lung | | |
| 22 | M | 50 | None | PD | Bone, lymph node, lung | | |
| 23 | M | 64 | R, C, I | N/A | Intraperitoneal, liver, lung | | |
| 24 | M | 62 | I | PR (1+ month) | Lung, intramuscular, skin | | |
| 25 | F | 61 | I | N/A | Lymph node | | |
| 26 | F | 61 | None | N/A | Lymph node | | |
| 27 | M | 21 | C, I | N/A | Unknown | | |
| 28 | F | 45 | R, C, I | N/A | Unknown | | |
| 29 | F | 63 | R, I | N/A | Lymph node, skin | | |
| 30 | F | 59 | I | N/A | Unknown | | |
| 31 | M | 56 | C, I | N/A | Unknown | | |
| 32 | M | 57 | I | N/A | Unknown | | |

[1] H = hormonal, R = radiotherapy, C = chemotherapy, I = immunotherapy
[2] PD = progressive disease, PR = partial response, SD = stable disease
[3] Patient response data is not available at this time.

Conclusion

This study demonstrated that clinical responses to anti-CTLA-4 antibody in combination with melanoma peptide vaccines strongly correlates with the occurrence of autoimmune-like adverse side-effects. Four of eight (50%) patients with autoimmune-like serious adverse effects had a clinical response. Only 2 of 28 patients (7%) had a response in the absence of any serious autoimmune-like adverse effect.

Example 4

Results from a Clinical Trial of Anti-CTLA-4 Antibody in Combination with the Approved Regimen for MELACINE®

Thirteen patients with malignant melanoma were administered anti-CTLA-4 antibody 10D1 (3 mg/kg×2 doses 8 weeks apart) in combination with the approved regimen for MELACINE® (including cyclophosphamide). No objective responses and no serious adverse events were observed.

Example 5

Statistical Analysis of the Results of Example 3 (a Clinical Trial of Anti-CTLA4 Antibody in Combination with gp100 Peptide Vaccines Six of the 38 patients had an objective tumor response. Four of these six responders (66.7%) had autoimmune serious adverse events. Only four of the 32 patients who did not respond had autoimmune serious adverse events (12.5%).

TABLE 5

Distribution of Autoimmune Serious Adverse Events (n = 38)

|  | Patients with Autoimmune SAE | Patients without Autoimmune SAE |
| --- | --- | --- |
| Non-responders | 4 | 28 |
| Responders | 4 | 2 |

A continuity-adjusted Chi-square test and Fisher's exact test were performed to examine the autoimmune incidence rate differed between responders and non-responders. A statistically significant correlation was found between patients that respond and patients that develop autoimmune serious adverse events using both the Chi-square test ($p=0.0146$) and the Fisher's exact test ($p=0.0116$).

Example 6

Statistical Analysis of the Results of Examples 2, 3 and 4

Eight of the 68 patients had an objective tumor response. Four of the eight responders (50%) had autoimmune serious adverse events. Only four of the 60 patients who did not respond (6.7%) had autoimmune serious adverse events.

TABLE 6

Distribution of Autoimmune Serious Adverse Events

|  | Patients with Autoimmune SAE | Patients without Autoimmune SAE |
| --- | --- | --- |
| Non-responders | 4 | 56 |
| Responders | 4 | 4 |

A continuity-adjusted Chi-square test and Fisher's exact test were performed to examine the autoimmune incidence rate difference between responders and non-responders. A statistically significant correlation was found between patients that respond and patients that develop autoimmune serious adverse events using both the Chi-square test ($p=0.0028$) and the Fisher's exact test ($p=0.0049$).

REFERENCES CITED

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

What is claimed is:

1. A method for treating cancer in a patient in need of such treatment, which method comprises administering an anti-CTLA-4 antibody in a dosage sufficient to induce a breakthrough event and detecting the breakthrough event.

2. The method of claim 1 wherein the breakthrough event is an autoimmune response.

3. The method of claim 1 wherein the breakthrough event is a severe, life-threatening, or disabling adverse event.

4. The method of claim 1, wherein the breakthrough event is induced by administering escalating doses of anti-CTLA-4 antibody.

5. The method of claim 1, wherein the breakthrough event is induced by administering anti-CTLA-4 at decreasing dosage intervals.

6. The method of claim 1, wherein the breakthrough event comprises a manifestation of non-tumor related autoimmunity.

7. The method of claim 1 wherein the cancer is an immunologically sensitive tumor.

8. The method of claim 1 wherein the cancer is malignant melanoma.

9. A method for treating melanoma in a patient in need of such treatment, which method comprises administering anti-CTLA-4 antibody 10D1 in a dosage sufficient to induce a breakthrough event and detecting the breakthrough event.

10. The method of claim 9 wherein the breakthrough event is an autoimmune response.

11. The method of claim 9 wherein the breakthrough event is a severe, life-threatening, or disabling adverse event.

12. The method of claim 11, wherein the breakthrough event is selected from the group consisting of diarrhea, enterocolitis, dermatitis, hypophysitis, panhypopituitarism, rash, and pruritis.

13. The method of claim 9, wherein the breakthrough event is induced by administering escalating doses of anti-CTLA-4 antibody.

14. The method of claim 9, wherein the breakthrough event is induced by administering anti-CTLA-4 at decreasing dosage intervals.

15. The method of claim 9, wherein the breakthrough event is selected from the group consisting of dermatitis, vitiligo, and enterocolitis.

16. The method of claim 1, where an additional therapeutic agent for treating the cancer is administered.

17. The method of claim 1, where an additional therapeutic agent for treating the breakthrough event is administered.

18. The method of claim 3, wherein the breakthrough event is selected from the group consisting of diarrhea, enterocolitis, dermatitis, hypophysitis, panhypopituitarism, rash, and pruritis.

19. The method of claim 1, wherein the breakthrough event is selected from the group consisting of dermatitis, vitiligo, and enterocolitis.

* * * * *

UNITED STATES PATENT AND TRADEMARK OFFICE
CERTIFICATE OF CORRECTION

| | | Page 1 of 1 |
|---|---|---|
| PATENT NO. | : 7,465,446 B2 | |
| APPLICATION NO. | : 10/857749 | |
| DATED | : December 16, 2008 | |
| INVENTOR(S) | : Lowy et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1059 days.

Signed and Sealed this
Twenty-third Day of August, 2011

David J. Kappos
*Director of the United States Patent and Trademark Office*